United States Patent
Mayorga et al.

(10) Patent No.: US 8,039,658 B2
(45) Date of Patent: Oct. 18, 2011

(54) REMOVAL OF TRACE ARSENIC IMPURITIES FROM TRIETHYLPHOSPHATE (TEPO)

(75) Inventors: Steven Gerard Mayorga, Oceanside, CA (US); Heather Regina Bowen, Vista, CA (US); Kelly Ann Chandler, San Marcos, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 735 days.

(21) Appl. No.: 12/179,979

(22) Filed: Jul. 25, 2008

(65) Prior Publication Data

US 2010/0018849 A1  Jan. 28, 2010

(51) Int. Cl.
*C07F 9/09* (2006.01)

(52) U.S. Cl. .......... 558/150; 558/87; 558/146; 210/660; 210/661; 210/681; 210/688; 438/478; 438/479; 438/480; 438/423

(58) Field of Classification Search .................. 210/660, 210/661, 681, 688; 558/150
See application file for complete search history.

(56) References Cited

U.S. PATENT DOCUMENTS 4,713,229 A * 12/1987 Schimmel et al. ......... 423/321.1
2011/0021803 A1 * 1/2011 Jin et al. ........................ 558/150

FOREIGN PATENT DOCUMENTS

| DE | 2644721 | 4/1978 |
|----|---------|--------|
| FR | 2762004 | 10/2008 |
| JP | 11050065 | 2/1999 |
| WO | 0076626 | 12/2000 |

OTHER PUBLICATIONS

Shigeru Maeda, et al, Iron (III) Hydroxide-Loaded Coral Limestone as an Adsorbent for Arsenic(III) and Arsenic (V), Separation and Science Technology, 1992, 681-9, 27(5).

B. Saha, et al, Physicochemical Characterization of Granular Ferric Hydroxide (GFH) for Arsenic(V) Sorption from Water, Separation Science and Technology, 2005, 2909-32, 40(14).

Ileana Rau, et al, Arsenic(V) adsorption by immobilized iron mediation. Modeling of the adsorption process and influence of interfering anions, Reactive & Functional Polymers, 2003, 85-94, 54(1-3).

V.M. Norwood III, et al, Removing heavy metals from phosphoric acid and phosphate fluid fertilizers, American Chemical Society Symposium Series, 1992, 147-60, 509.

Heinz Spindler, et al, Sorptive Purification of Acetylene, Chemie Ingenieur Technik, 2002, 1595-1600, 74(11).

* cited by examiner

*Primary Examiner* — Glenn Caldarola
*Assistant Examiner* — Michelle Stein
(74) *Attorney, Agent, or Firm* — Lina Yang

(57) ABSTRACT

A method of removing trace levels of arsenic-containing impurities from raw triethylphosphate (TEPO) is disclosed. The method uses adsorption, or adsorption followed by a flash distillation. The method comprises contacting raw triethylphosphate (TEPO) with an adsorbent which selectively adsorbs the arsenic-containing impurities in the raw triethylphosphate (TEPO). The adsorbent is a base promoted alumina containing adsorbent represented by a formula: $Z_x W_y$; where x is the weight percentage of Z in the adsorbent ranging from 30% to 99.999%; y is the weight percentage of W in the adsorbent, and x+y=100%; Z is selected from the group consisting of alumina ($Al_2O_3$), magnesium-alumina based layered double hydroxide (MgO—$Al_2O_3$), alumina-zeolite, and mixtures thereof; and W is selected from the group consisting of at least one basic metal oxide, at least one basic metal carbonate, and mixtures thereof. The method will result in a final triethylphosphate (TEPO) with a few ppb to less than 1 ppb arsenic containing impurities.

25 Claims, No Drawings

REMOVAL OF TRACE ARSENIC IMPURITIES FROM TRIETHYLPHOSPHATE (TEPO)

BACKGROUND OF THE INVENTION

Triethylphosphate (TEPO) is a liquid chemical commonly used as the phosphorous-containing source for the production of PSG (phosphosilicate glass) or BPSG (borophosphosilicate glass) in the microelectronics industry. PSG and BPSG are used in semiconductor devices as insulating layers that are deposited between metal or conducting layers. BPSG films are typically used as planarization films which can provide excellent step coverage for high density microelectronic devices. The presence of percent levels of boron and phosphorus in the BPSG films has the effect of decreasing the glass transition temperature relative to the silicate glass, thus decreasing the thermal budget of a fabrication process while providing gap-filling properties that enable the BPSG layer to meet the requirements of microelectronic manufacturing processes.

Manufacturers require phosphorous sources, such as TEPO, to be extremely pure with respect to certain metals such as arsenic and other metals. Certain metallic impurities may act as device poisons or have undesirable toxicological properties, especially in the case of arsenic, that may present significant environmental health and safety issues during the normal life cycle of the device, such as during manufacturing or waste disposal after use.

For the aforementioned reasons, manufacturers in the microelectronics industry require that TEPO meets very stringent specifications with respect to the concentration of certain metallic impurities. Typical concentration specifications for TEPO require that many alkali, alkaline earth, rare earth, transition and main group metals are present at less than 5 ppb, or more commonly less than 1-3 ppb.

However, raw TEPO has arsenic levels of 50 ppb (parts per billion) to over 10,000 ppb depending on the particular source and how it was processed. Achieving arsenic levels of less than 5 ppb, or more commonly less than 1-3 ppb, presents a substantial challenge for arsenic in particular, which is a common impurity in phosphorus-containing materials.

The removal of trace levels (about 50 ppb to 10,000 ppb) of arsenic impurities from TEPO often cannot be accomplished by the use of common separation techniques because of the similarity in the chemical and physical properties of the phosphorus and arsenic compounds.

There are numerous examples in the prior art of the removal of arsenic-containing impurities from various systems, including gaseous streams such as acetylene or silane, liquid hydrocarbon fractions used in the petrochemical industry, aqueous systems, and phosphate based fluid fertilizer streams. The arsenic-containing components removed during processing are either tri-valent or penta-valent, and either organic and inorganic.

The majority of the previous works described the removal of arsenic such that the treated material had a final arsenic content of 1-1000 ppm (parts per million, 1 ppm=1000 ppb). The description of the removal of arsenic to ultra-trace levels (10 ppb or less) found in the prior art was for the preparation of high purity silane used for microelectronic applications. In the latter case the primary arsenic contaminant is gaseous arsine, as opposed to the present disclosure in which the arsenic impurities are believed to be either miscible liquids, such as triethylarsenate (TEASAT) or solubilized inorganic salts.

BRIEF SUMMARY OF THE INVENTION

Therefore, a method of achieving the low level of arsenic in TEPO required by semiconductor manufacturers is needed.

According to one embodiment of the invention, a method of removing arsenic-containing impurities from raw triethylphosphate (TEPO) having the arsenic-containing impurities, comprises:
  providing an adsorbent selective to adsorb the arsenic-containing impurities in comparison with triethylphosphate;
  contacting the raw triethylphosphate having the arsenic-containing impurities with the adsorbent; and
  adsorbing the arsenic-containing impurities from the raw triethylphosphate having the arsenic-containing impurities to produce a product triethylphosphate having reduced arsenic-containing impurities.

According to another embodiment of the invention, a method of removing arsenic-containing impurities from raw triethylphosphate having the arsenic-containing impurities comprises:
  providing an adsorbent selective to adsorb the arsenic-containing impurities in comparison with triethylphosphate;
  contacting the raw triethylphosphate having the arsenic-containing impurities with the adsorbent; and
  adsorbing the arsenic-containing impurities from the raw triethylphosphate having the arsenic-containing impurities to produce a product triethylphosphate having reduced arsenic-containing impurities; and
  distilling the product triethylphosphate having reduced arsenic-containing impurities to further remove the arsenic-containing impurities from the product triethylphosphate having reduced arsenic-containing impurities.

According to yet one another embodiment of the invention, a method of removing arsenic-containing impurities from raw triethylphosphate having the arsenic-containing impurities comprising:
  providing an adsorbent selective to adsorb the arsenic-containing impurities in comparison with triethylphosphate;
  contacting the raw triethylphosphate having the arsenic-containing impurities with the adsorbent; and
  adsorbing the arsenic-containing impurities from the raw triethylphosphate having the arsenic-containing impurities to produce a product triethylphosphate having reduced arsenic-containing impurities; and
  distilling the product triethylphosphate having reduced arsenic-containing impurities to further remove the arsenic-containing impurities, and remove volatile organic byproducts and non-volatile residual metallic impurities from the product triethylphosphate having reduced arsenic-containing impurities.

In the embodiments above, the adsorbent is a base promoted alumina containing adsorbent represented by a formula: $Z_xW_y$, where
  x is the weight percentage of Z in the adsorbent ranging from 30% to 99.999%;
  y is the weight percentage of W in the adsorbent, and x+y=100%;
  Z is selected from the group consisting of alumina ($Al_2O_3$), magnesium-alumina based layered double hydroxide ($MgO$—$Al_2O_3$), alumina-zeolite, and mixtures thereof; and W is selected from the group consisting of at least one basic metal oxide, at least one basic metal carbonate, and mixtures thereof.

The embodiments above can further include activating the adsorbent through heating under vacuum or a dry inert gas atmosphere, before contacting step.

DETAILED DESCRIPTION OF THE INVENTION

Triethylphosphate (TEPO) is an important liquid used as a precursor for the production of PSG (phosphosilicate glass) or BPSG (borophosphosilicate glass) used in semiconductor devices as insulating layers that are deposited between metal or conducting layers. The purity of the TEPO, especially for the most demanding electronic applications, is of importance for providing the proper electrical properties in PSG or BPSG formed from that TEPO. Minimization of the toxic impurities is also of importance to address increasing concerns about environmental, health and safety issues related to the product use and overall life-cycle.

Since impurities in the TEPO precursor are captured in the PSG or BPSG thin film, the purity of the TEPO precursor is important. Certain impurities, namely arsenic, and alkali metals are especially harmful to the end-product use as they cannot be removed by bulk processing methods commonly used in the semiconductor industry. Microelectronic device manufacturers require that these deleterious metals be present at concentrations no greater than several parts per billion (ppb) to ensure appropriate performance of their films and to minimize environmental, health and safety issues associated with high toxicity of residual arsenic.

In order to understand the origin of the arsenic contamination in TEPO one must consider its entire synthesis history. TEPO is made from the reaction of ethanol with phosphoryl chloride ($POCl_3$). Phosphoryl chloride is itself produced from phosphorous trichloride ($PCl_3$), which in turn is made from white phosphorus ($P_4$), which is made from phosphate rock, according to the reaction sequence outlined below:

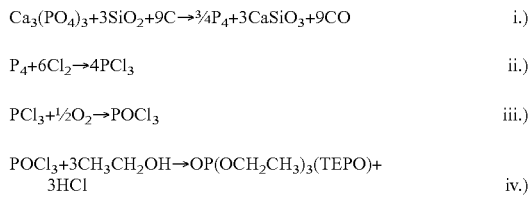

$Ca_3(PO_4)_3 + 3SiO_2 + 9C \rightarrow \frac{3}{4}P_4 + 3CaSiO_3 + 9CO$     i.)

$P_4 + 6Cl_2 \rightarrow 4PCl_3$     ii.)

$PCl_3 + \frac{1}{2}O_2 \rightarrow POCl_3$     iii.)

$POCl_3 + 3CH_3CH_2OH \rightarrow OP(OCH_2CH_3)_3 (TEPO) + 3HCl$     iv.)

Phosphate rock typically contains 0.01% to 0.1% arsenic relative to phosphorus. The chemistry and chemical reactivity of arsenic is similar to that of phosphorus. Thus, low levels of arsenic present in the phosphate rock source material are readily converted to yellow arsenic ($As_4$), to arsenic trichloride ($AsCl_3$), to arsenic oxychloride ($AsOCl_3$), and finally to triethylarsenate ($OAs(OCH_2CH_3)_3$), also known as TEASAT. Consequently, raw TEPO is invariably contaminated with high ppb or ppm levels of arsenic impurities typically present as TEASAT. The amount of TEASAT in the raw TEPO depends on a number of factors including the arsenic content of the original phosphorus starting material, the synthetic history, and the post-synthetic processing.

A common way to purify raw TEPO is by fractional distillation. Distillation very effectively separates the TEPO from volatile organic byproducts and from non-volatile residual metallic impurities. However, it is far less effective at achieving quantitative removal of TEASAT, the arsenic analog of TEPO, and main source of the arsenic impurity. TEASAT is volatile and has a normal boiling point of 236° C., as compared to the boiling point of TEPO of 216° C. This similarity in boiling points makes it exceeding difficult to achieve quantitative separation of TEASAT from TEPO by fractional distillation methods. Even so, it has been demonstrated that very low levels of arsenic (i.e., <5 ppb) can be realized by subjecting the raw TEPO to multiple fractional distillation. Such processing methods may involve 2, 3 or even 4 successive distillations in order to attain the desired low ppb levels of arsenic required by manufacturers in the microelectronics industry. This involves multiple unit operations, and as such, is very time consuming and often prohibitively expensive.

There would be a clear advantage to the use of a passive purification method, such as adsorption, to reduce the arsenic in TEPO to the target concentration level. The present disclosure teaches adsorbents and processes that can be utilized to remove the arsenic impurities from TEPO to very low levels. A number of adsorbents and classes of adsorbents are identified which work very effectively for this purpose. The arsenic purification method described herein uses basic adsorbents to remove the majority of the arsenic-containing components. A distillation polishing step can be used to remove the residual arsenic components, such as inorganic arsenic salts, to produce TEPO with ultra-trace levels of arsenic.

In the present invention base promoted alumina containing (BPAC) adsorbents can be used to remove arsenic impurities from TEPO. This category of adsorbents contains alumina that exists either as $Al_2O_3$ or as a mixed metal oxide or mixed metal hydroxide compound, wherein the said alumina-containing entity has been modified by a basic component such as a basic metal oxide and/or a basic metal carbonate.

The composition of the BPAC adsorbents is represented by a formula: $Z_xW_y$, where x is the weight percentage of Z in the adsorbent ranging from 30% to 99.999%, y is the weight percentage of W in the adsorbent, x+y=100%, Z is selected form the group consisting of alumina ($Al_2O_3$), magnesium-alumina based layered double hydroxide (MgO—$Al_2O_3$), and alumina-zeolite, and W is selected from the group consisting of at least one basic metal oxide, at least one basic metal carbonate, and the mixtures thereof. Examples of W are MgO, CaO, $Na_2O$, $K_2O$, $K_2CO_3$, $Na_2CO_3$, and mixtures thereof.

The base promoted alumina containing (BPAC) adsorbents are shown to be very effective for reducing the arsenic content in TEPO to low ppb levels. High surface area alumina adsorbents that possess a weakly or strongly basic surface, and basic mixed metal oxide materials exhibit the best ability to scavenge the arsenic species from TEPO solution.

Examples of such BPAC adsorbents include, but are not limited to: (1) MgO—$Al_2O_3$ blends, (2) alkali metal carbonate promoted MgO—$Al_2O_3$ blends, (3) alumina modified with trace levels (10 ppm to 100 ppm) to percent levels (about 20% or greater) of basic alkali metals oxides such as $Na_2O$ or $K_2O$, (4) alumina modified with trace levels (10 ppm to 100 ppm) to percent levels (about 20% or greater) of alkali metal carbonates such as $Na_2CO_3$ or $K_2CO_3$, and (5) alumina-zeolite blends, modified with basic components such as alkali metal oxides or alkali metal carbonates.

The BPAC adsorbents can be prepared by a number of different methods including, but not limited to: (1) treatment of the porous alumina support with an aqueous solution containing the dissolved alkali metal carbonate or alkali metal carbonate precursor, using well known soak or spray-on impregnation techniques, followed by calcination at the appropriate temperature to form the desired BPAC adsorbent; or (2) co-forming the desired alumina/akali metal carbonate or alumina/alkali metal oxide by co-precipitating or co-depositing the appropriate blend of precursor materials, that, upon subsequent calcination, yields the desired co-formed mixed metal oxide or mixed metal oxycarbonate.

The adsorptive removal of the arsenic can be achieved either by contacting the arsenic-laiden TEPO to the adsorbent media under static conditions, or alternatively, by contacting the said TEPO with the adsorbent by flowing the liquid through a column packed with the adsorbent media under dynamic exposure conditions. The optimal conditions for arsenic removal would depend on the chemical nature and concentration of the arsenic impurities and the required arsenic content of the purified TEPO. The contact or residence time will range from as low as several minutes for those embodiments that use dynamic conditions such as a packed column of adsorbent media, or alternatively, up to several days for those embodiments that utilize static adsorption conditions. The temperature used during the contacting step may range from 0° C. to 140° C., or from 20° C. to 80° C.

Static adsorption involves exposing the arsenic-laiden TEPO to a given amount of adsorbent material at a predetermined temperature for an effective period of time to accomplish the desired reduction in arsenic level. The amount of adsorbent may range from a fraction of a percent to over 20 wt. % on a total weight basis, total weight is the sum of the weight of the adsorbent and the weight of TEPO. The adsorption temperature may range from sub-ambient to temperatures in excess of 100° C. Lower temperatures tend to favor improved selectivity which often results in a higher arsenic equilibrium adsorption capacity, while the higher temperatures favor improved adsorption rate of the arsenic impurities. The required time for static adsorption may vary from as little as several hours to several days depending on a number of factors including: (1) the weight % loading of the adsorbent; (2) the adsorption temperature; (3) the arsenic concentration of the feed stream; (4) the chemical nature of the arsenic contaminants; and (5) the desired arsenic concentration of the processed TEPO. Numerous examples of the use of static adsorption methods to remove arsenic are provided in this disclosure.

Dynamic adsorption can also be employed to achieve the reduction of arsenic to the desired low ppb levels in TEPO. This can be accomplished by contacting the TEPO containing the unwanted arsenic with a solid state adsorbent such as a porous alumina that contains basic sites or a basic mixed metal oxide adsorbent. This method typically involves passing the subject liquid through a column containing a fixed bed of adsorbent material. The arsenic-containing species are subsequently sequestered by the basic sites on the adsorbent bed, thus rendering the treated liquid with low ppb levels of residual arsenic.

The base promoted alumina containing (BPAC) adsorbents used to remove arsenic-containing impurities from TEPO are summarized in Table 1 with respect to their chemical composition and structure, reference name, and their physical form. Examples of commercial sources of representative materials are also provided in Table 1.

The arsenic content of said TEPO can be reduced from over 80 ppb to 1-5 ppb by exposing the TEPO to various loadings of the said BPAC adsorbents under static exposure conditions for periods of several hours to several days, in the temperature range of 20-80° C. Subsequent distillation of the adsorbent treated TEPO may be required to further reduce the arsenic content to <1 ppb, or to reduce the concentration of other undesired metallic impurities.

In some embodiments, the adsorbent is first activated prior to contact with the TEPO to effect arsenic removal. In the said embodiments, the adsorbent is heated to one or more temperatures that is 80° C. or greater. Preferably, the heating step is conducted to one or more temperatures that range from about 80° C. to about 600° C., or from about 100° C. to about 500° C., or from about 200° C. to about 400° C. The required activation temperature of the adsorbent precursor depends on the specific chemical and physical nature of the adsorbent. The optimal activation temperature and conditions can be ascertained by thermal gravimetric analysis (TGA) or other means. The heating may be performed under vacuum or alternatively within a dry, inert atmosphere, such as $N_2$, He, or Ar.

TABLE 1

Adsorbents evaluated

| Adsorbent Reference | Chemical Composition | | | Example of Commercial Adsorbent | |
|---|---|---|---|---|---|
| | Composition | Structure/ Morphology | Physical Form | Product Name | Company |
| BPAC-1 | 70% MgO, 30% $Al_2O_3$ | layered double hydroxide with excess MgO | 1/8" pellets | MG70 | Sasol |
| BPAC-2 | $Al_2O_3$ with trace levels of basic metal oxides | porous alumina | 1/16" beads | alumina spheres | Sasol |
| BPAC-3 | 9 wt. % $Na_2O$ on $Al_2O_3$ | porous alumina impregnated with metal oxide | 1/16" beads | CL-750 | BASF |
| BPAC-4 | 5 wt. % $Na_2O$ on $Al_2O_3$ | porous alumina impregnated with metal oxide | 1/16" beads | DD-710 | BASF |
| BPAC-5 | 5 wt. % $K_2CO_3$ on $Al_2O_3$ | porous alumina impregnated with metal carbonate | 1/16" beads | AA-320 | Alcan |
| BPAC-6 | $Na_2CO_3$ on $Al_2O_3$-ZeoliteY | alumina-zeolite blend containing metal carbonate | 1/16" beads | SS-Golden | Alcan |
| BPAC-7 | 8 wt. % $Na_2CO_3$ on $Al_2O_3$ | porous alumina co-formed with metal carbonate | 1/16" beads | AA-230 | Alcan |
| BPAC-8 | 8 wt. % $K_2CO_3$ on $Al_2O_3$ | porous alumina co-formed with metal carbonate | 1/16" beads | AA-330 | Alcan |

TABLE 1-continued

Adsorbents evaluated

| Adsorbent Reference | Chemical Composition | | | Example of Commercial Adsorbent | |
|---|---|---|---|---|---|
| | Composition | Structure/ Morphology | Physical Form | Product Name | Company |
| BPAC-9 | 20/56/24 mixture of $K_2CO_3$—MgO—$Al_2O_3$ | Mg—Al layered double hydroxide promoted with metal carbonate | 1/16" beads | Puralox MG70 ($K_2CO_3$) | Sasol |
| BPAC-10 | MgO•$(K_2CO_3)_2$ on $Al_2O_3$ | alumina impregnated with Mg—Al oxycarbonate | 1/16" beads | NA | NA |
| IE-1 | dimethyamino functionality | ion exchange resin for non-aqueous systems | beads | Amberlite A-21 ion exchange resin | Rohm and Haas |
| AC-1 | carbon | activated porous carbon | granules | Puraspec | Johnson Matthey Group |
| SG-1 | $SiO_2$ | amorphous silica gel | granules | Silica gel, grade 635-645 | Davisil |

BPAC = Base promoted alumina containing;
IE = Ion exchange;
AC = Activated Carbon; and
SG = silica gel The arsenic-containing components in TEPO or decomposition products of the arsenic-containing components are believed to preferentially adsorb or react with the surface of the adsorbent such that the arsenic species become physi-sorbed or chemi-sorbed to the adsorbent surface. The adsorbents of the present invention reduce the amount of arsenic within the incoming raw TEPO liquid to about 20 ppb or below, preferably 10 ppb or below, more preferably 3 ppb, or most preferably 1 ppb or below.

Following the adsorption treatment of the TEPO to remove arsenic, distillation may be used. Distillation very effectively separates the TEPO from volatile organic byproducts and from non-volatile residual metallic impurities. Distillation is also used as a final polishing step to remove residual metallic impurities such as those that may have been leached into the TEPO as a consequence of contact of the TEPO liquid with the solid adsorbent media. Low ppb levels of certain metals such as alkali, alkaline earth, rare earth, transition and main group metals may be extracted into the TEPO either as dissolved species or as solid particulates as a consequence of the contact of the TEPO liquid with the adsorbent media. Either the dissolved or particulate species which may contain the metal components are expected to be non-volatile, and as such, can be readily separated from the parent TEPO solution by typical distillation methods. This final distillation polishing step may be employed to ensure that metals present at trace levels in the solid adsorbent do not contaminate the TEPO with unacceptable levels of said metals.

Additional objects, advantages, and novel features of this invention will become apparent to those skilled in the art upon examination of the following examples thereof, which are not intended to be limiting.

WORKING EXAMPLES

Example 1

Activation of Adsorbents BPAC-1 Through BPAC-8

Adsorbents BPAC-1 and BPAC-2 were activated by the manufacturer at 600° C. under nitrogen prior to shipment. Adsorbents BPAC-3 through BPAC-8 were activated on site by heating in a laboratory oven to 200° C. for 20 hours under flowing nitrogen prior to use. Further description about the chemical composition, structure and physical form of these adsorbents is provided in Table 1. After thermal activation, all adsorbents were stored in a nitrogen-purged glovebox until needed for the adsorption studies described in the examples below.

Example 2

Removal of Trace Arsenic From TEPO Using Adsorbent BPAC-1

An adsorbent consisting of a 70:30 mixture of MgO and $Al_2O_3$ was used for this experiment. This adsorbent is referred to herein as BPAC-1. Working within a nitrogen glovebox, 45.0 g of TEPO and 5.0 g of adsorbent BPAC-1 were placed sequentially into each of two 100 ml Pyrex bottles. The TEPO was previously analyzed to contain 76 ppb of arsenic by ICP-MS (inductively coupled plasma-mass spectroscopy). BPAC-1 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots (4 mls) were taken for arsenic analysis after one and three days storage at ambient temperature, and after one and two days storage at 80° C. The analysis showed that the arsenic content in the TEPO dropped from an initial value of 76 ppb to 19 ppb after three days at ambient temperature, and from 76 ppb to 25 ppb after two days at 80° C. The data are summarized in Table 2.

Example 3

Removal of Trace Arsenic from TEPO Spiked with TEASAT Using Adsorbent BPAC-1

TEPO spiked with 30 ppb of arsenic as TEASAT (triethylarsenate) was used for this example. This sample of TEPO was analyzed to contain 117 ppb of arsenic. Working within a nitrogen glovebox, 45.0 g of TEPO and 5.0 g of adsorbent BPAC-1 were placed sequentially into each of two 100 ml Pyrex bottles. BPAC-1 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken for arsenic analysis after one and three storage at ambient temperature, and after one and two days storage at 80° C. The analysis showed that the arsenic content in the TEPO dropped from an initial value of 117 ppb to 33 ppb after three days at ambient temperature, and from 117 ppb to 27 ppb after two days at 80° C. The data are summarized in Table 2.

Example 4

Removal of Trace Arsenic from TEPO Using Adsorbent BPAC-2

An adsorbent consisting of $Al_2O_3$ with trace levels of several basic metal oxides was used for this experiment. This adsorbent is referred to herein as BPAC-2. Working within a nitrogen glovebox, 45.0 g of TEPO and 5.0 g of adsorbent BPAC-2 were placed sequentially into each of two 100 ml Pyrex bottles. The TEPO was previously analyzed to contain 76 ppb of arsenic by ICP-MS. BPAC-2 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken for arsenic analysis after one and three days storage at ambient temperature, and after one and two days storage at 80° C. The analysis showed that the arsenic content in the TEPO dropped from an initial value of 76 ppb to 6.4 ppb after three days at ambient temperature, and from 76 ppb to 5.3 ppb after two days at 80° C. The data are summarized in Table 2.

Example 5

Removal of Trace Arsenic from TEPO Spiked with TEASAT Using Adsorbent BPAC-2

TEPO spiked with 30 ppb of arsenic as TEASAT was used for this example. This sample of TEPO was analyzed to contain 117 ppb of arsenic. Working within a nitrogen glovebox, 45.0 g of TEPO and 5.0 g of adsorbent BPAC-2 were placed sequentially into each of two 100 ml Pyrex bottles. BPAC-2 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken for arsenic analysis after storage at ambient temperature, and after one and two days storage 80° C. The analysis showed that the arsenic content in the TEPO dropped from an initial value of 117 ppb to 10.5 ppb after three days at ambient temperature, and from 117 ppb to 8.3 ppb after two days at 80° C. The data are summarized in Table 2.

Example 6

Removal of Trace Arsenic from TEPO Using Adsorbent BPAC-3

An adsorbent consisting of 9 wt. % $Na_2O$ on $Al_2O_3$ was used for this experiment. This adsorbent is referred to herein as BPAC-3. Working within a nitrogen glovebox, 27.0 g of TEPO and 3.0 g of adsorbent BPAC-3 were placed sequentially into each of two 100 ml Pyrex bottles. The TEPO was previously analyzed to contain 76 ppb of arsenic by ICP-MS. BPAC-3 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 76 ppb to 7.1 ppb and 15.0 ppb for the samples exposed to adsorbent for two days at ambient temperature and 80° C., respectively. The data are summarized in Table 2.

Example 7

Removal of Trace Arsenic from TEPO Spiked with TEASAT Using Adsorbent BPAC-3

TEPO spiked with 30 ppb of arsenic as TEASAT was used for this example. This sample of TEPO was analyzed to contain 117 ppb of arsenic. Working within a nitrogen glovebox, 27.0 g of TEPO and 3.0 g of adsorbent BPAC-3 were placed sequentially into each of two 100 ml Pyrex bottles. BPAC-3 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 117 ppb to 8.5 ppb and 16.3 ppb for the samples exposed to adsorbent for two days at ambient temperature and 80° C., respectively. The data are summarized in Table 2.

Example 8

Removal of Trace Arsenic from TEPO Using Adsorbent BPAC-4

An adsorbent consisting of 5 wt. % $Na_2O$ on $Al_2O_3$ was used for this experiment. This adsorbent is referred to herein as BPAC-4. Working within a nitrogen glovebox, 27.0 g of TEPO and 3.0 g of adsorbent BPAC-4 were placed sequentially into each of two 100 ml Pyrex bottles. The TEPO was previously analyzed to contain 76 ppb of arsenic by ICP-MS. BPAC-4 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 76 ppb to 4.9 ppb and 6.5 ppb for the samples exposed to adsorbent for two days at ambient temperature and 80° C., respectively. The data are summarized in Table 2.

Example 9

Removal of Trace Arsenic from TEPO Spiked with TEASAT Using Adsorbent BPAC-4

TEPO spiked with 30 ppb of arsenic as TEASAT was used for this example. This sample of TEPO was analyzed to contain 117 ppb of arsenic. Working within a nitrogen glovebox, 27.0 g of TEPO and 3.0 g of adsorbent BPAC-4 were placed sequentially into each of two 100 ml Pyrex bottles. BPAC-4 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 117 ppb to 5.9 ppb and 7.8 ppb for the samples exposed to adsorbent for two days at ambient temperature and 80° C., respectively. The data are summarized in Table 2.

TABLE 2

Static Adsorption Experiments (BPAC-1 through BPAC-4)

| Example No. | Adsorbent | TEPO Soure | Temp | Scale (g) | Adsorbent loading (wt. %) | Time (hours) | Arsenic conc. (ppb) | Arsenic capacity (μg/g ads) |
|---|---|---|---|---|---|---|---|---|
| 2 | BPAC-1 | TEPO (76 ppb As) | 22° C. | 45.0 | 0.0 | 0 | 75.8 | NA |
| | | | | 50.0 | 10.0 | 24 | 25.8 | 0.45 |
| | | | | 50.0 | 10.0 | 72 | 18.9 | 0.51 |
| | | | 80° C. | 45.0 | 0.0 | 0 | 75.8 | NA |
| | | | | 50.0 | 10.0 | 24 | 27.9 | 0.43 |
| | | | | 50.0 | 10.0 | 48 | 25.2 | 0.46 |
| 3 | | TEPO (117 ppb As) | 22° C. | 45.0 | 0.0 | 0 | 117.3 | NA |
| | | | | 50.0 | 10.0 | 24 | 55.5 | 0.56 |
| | | | | 50.0 | 10.0 | 72 | 33.3 | 0.76 |
| | | | 80° C. | 45.0 | 0.0 | 0 | 117.3 | NA |
| | | | | 50.0 | 10.0 | 24 | 53.2 | 0.58 |
| | | | | 50.0 | 10.0 | 48 | 27.0 | 0.81 |
| 4 | BPAC-2 | TEPO (76 ppb As) | 22° C. | 45.0 | 0.0 | 0 | 75.8 | NA |
| | | | | 50.0 | 10.0 | 24 | 7.9 | 0.61 |
| | | | | 50.0 | 10.0 | 72 | 6.4 | 0.62 |
| | | | 80° C. | 45.0 | 0.0 | 0 | 75.8 | NA |
| | | | | 50.0 | 10.0 | 24 | 6.8 | 0.62 |
| | | | | 50.0 | 10.0 | 48 | 5.3 | 0.63 |
| 5 | | TEPO (117 ppb As) | 22° C. | 45.0 | 0.0 | 0 | 117.3 | NA |
| | | | | 50.0 | 10.0 | 24 | 11.5 | 0.95 |
| | | | | 50.0 | 10.0 | 72 | 10.5 | 0.96 |
| | | | 80° C. | 45.0 | 0.0 | 0 | 117.3 | NA |
| | | | | 50.0 | 10.0 | 24 | 11.4 | 0.95 |
| | | | | 50.0 | 10.0 | 48 | 8.3 | 0.98 |
| 6 | BPAC-3 | TEPO (76 ppb As) | 22° C. | 27.0 | 0.0 | 0 | 75.8 | NA |
| | | | | 30.0 | 10.0 | 24 | 17.5 | 0.52 |
| | | | | 30.0 | 10.0 | 48 | 7.1 | 0.62 |
| | | | 80° C. | 27.0 | 0.0 | 0 | 75.8 | NA |
| | | | | 30.0 | 10.0 | 24 | 23.1 | 0.47 |
| | | | | 30.0 | 10.0 | 48 | 15.0 | 0.55 |
| 7 | | TEPO (117 ppb As) | 22° C. | 27.0 | 0.0 | 0 | 117.3 | NA |
| | | | | 30.0 | 10.0 | 24 | 25.1 | 0.83 |
| | | | | 30.0 | 10.0 | 48 | 8.5 | 0.98 |
| | | | 80° C. | 27.0 | 0.0 | 0 | 117.3 | NA |
| | | | | 30.0 | 10.0 | 24 | 29.9 | 0.79 |
| | | | | 30.0 | 10.0 | 48 | 16.3 | 0.91 |
| 8 | BPAC-4 | TEPO (76 ppb As) | 22° C. | 27.0 | 0.0 | 0 | 75.8 | NA |
| | | | | 30.0 | 10.0 | 24 | 8.3 | 0.61 |
| | | | | 30.0 | 10.0 | 48 | 4.9 | 0.64 |
| | | | 60° C. | 27.0 | 0.0 | 0 | 75.8 | NA |
| | | | | 30.0 | 10.0 | 24 | 6.5 | 0.62 |
| 9 | | TEPO (117 ppb As) | 22° C. | 27.0 | 0.0 | 0 | 117.3 | NA |
| | | | | 30.0 | 10.0 | 24 | 6.4 | 1.00 |
| | | | | 30.0 | 10.0 | 48 | 5.9 | 1.00 |
| | | | 60° C. | 27.0 | 0.0 | 0 | 117.3 | NA |
| | | | | 30.0 | 10.0 | 24 | 7.8 | 0.99 |

Example 10

Removal of Trace Arsenic from TEPO Using Adsorbent BPAC-5

An adsorbent consisting of 5 wt. % $K_2CO_3$ on $Al_2O_3$ was used for this experiment. This adsorbent is referred to herein as BPAC-5. Working within a nitrogen glovebox, 27.0 g of TEPO and 3.0 g of adsorbent BPAC-5 were placed sequentially into each of two 100 ml Pyrex bottles. The TEPO was previously analyzed to contain 76 ppb of arsenic by ICP-MS. BPAC-5 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 76 ppb to 9.0 ppb and 14.1 ppb for the samples exposed to adsorbent for two days at ambient temperature and 80° C., respectively. The data are summarized in Table 3.

Example 11

Removal of Trace Arsenic from TEPO Spiked with TEASAT Using Adsorbent BPAC-5

TEPO spiked with 30 ppb of arsenic as TEASAT was used for this example. This sample of TEPO was analyzed to contain 117 ppb of arsenic. Working within a nitrogen glovebox, 27.0 g of TEPO and 3.0 g of adsorbent BPAC-5 were placed sequentially into each of two 100 ml Pyrex bottles. BPAC-5 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 117 ppb to 15.5 ppb and 20.6 ppb for the samples exposed to adsorbent for two days at ambient temperature and 80° C., respectively. The data are summarized in Table 3.

Example 12

Removal of Trace Arsenic from TEPO Using Adsorbent BPAC-6

An adsorbent consisting of a mixture of $Al_2O_3$ and Zeolite Y modified with $Na_2CO_3$ was used for this experiment. This adsorbent is referred to herein as BPAC-6. Working within a nitrogen glovebox, 27.0 g of TEPO and 3.0 g of adsorbent BPAC-6 were placed sequentially into each of two 100 ml Pyrex bottles. The TEPO was previously analyzed to contain 76 ppb of arsenic by ICP-MS. BPAC-6 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 76 ppb to 8.1 ppb and 7.2 ppb for the samples exposed to adsorbent for two days at ambient temperature and 80° C., respectively. The data are summarized in Table 3.

Example 13

Removal of Trace Arsenic from TEPO Spiked with TEASAT Using Adsorbent BPAC-6

TEPO spiked with 30 ppb of arsenic as TEASAT was used for this example. This sample of TEPO was analyzed to contain 117 ppb of arsenic. Working within a nitrogen glovebox, 27.0 g of TEPO and 3.0 g of adsorbent BPAC-6 were placed sequentially into each of two 100 ml Pyrex bottles. BPAC-6 was previously activated as described in Example 1. The bottles were capped with Teflon-coated lids, and were periodically agitated over the course of one hour by swirling the liquid to ensure that the adsorbent pellets were uniformly wetted. One bottle was left in the glovebox at ambient temperature; the other bottle was placed into an oven pre-heated to 80° C. Small aliquots were taken from each of the two bottles after one day and after two days for arsenic analysis by ICP-MS. The analysis showed that the arsenic content in the TEPO dropped from an initial value of 117 ppb to 11.1 ppb and 9.7 ppb for the samples exposed to adsorbent for two days at ambient temperature and 80° C., respectively. The data are summarized in Table 3.

Example 14

Removal of Trace Arsenic from TEPO Using Adsorbent BPAC-7

An adsorbent consisting of $Al_2O_3$ coformed with 8 wt. % $Na_2CO_3$ was used for this experiment. This adsorbent is referred to herein as BPAC-7. Working within a nitrogen glovebox, 27.0 g of TEPO and 3.0 g of adsorbent BPAC-7 were placed sequentially into each of two 100 ml Pyrex bottles. The TEPO was previously analyzed to contain 76 ppb of arsenic by ICP-MS. BPAC-7 was previously activated as described in Example 1. The bottle was capped with a Teflon-coated lid, and was periodically agitated over the course of one hour by swirling the liquid to ensure that the adsorbent pellets were uniformly wetted. The bottle was left in the glovebox at ambient temperature. Small aliquots were taken after one day and after two days for arsenic analysis by ICP-MS. The analysis showed that the arsenic content in the TEPO dropped from an initial value of 76 ppb to 10.0 ppb after exposure to adsorbent for two days at ambient temperature. The data are summarized in Table 3.

Example 15

Removal of Trace Arsenic from TEPO Using Adsorbent BPAC-8

An adsorbent consisting of $Al_2O_3$ coformed with 8 wt. % $K_2CO_3$ was used for this experiment. This adsorbent is referred to herein as BPAC-8. Working within a nitrogen glovebox, 27.0 g of TEPO and 3.0 g of adsorbent BPAC-8 were placed sequentially into a 100 ml Pyrex bottle. BPAC-8 was previously activated as described in Example 1. The TEPO was previously analyzed to contain 76 ppb of arsenic by ICP-MS. The bottle was capped with a Teflon-coated lid, and was periodically agitated over the course of one hour by swirling the liquid to ensure that the adsorbent pellets were uniformly wetted. The bottle was left in the glovebox at ambient temperature. Small aliquots were taken after one day and after two days for arsenic analysis by ICP-MS. The analysis showed that the arsenic content in the TEPO dropped from an initial value of 76 ppb to 12.5 ppb after exposure to adsorbent for two days at ambient temperature. The data are summarized in Table 3.

TABLE 3

Static Adsorption Experiments (BPAC-5 through BPAC-8)

| Example No. | Adsorbent | TEPO Source | Temp | Scale (g) | Adsorbent loading (wt. %) | Time (hours) | Arsenic conc. (ppb) | Arsenic capacity (µg/g ads) |
|---|---|---|---|---|---|---|---|---|
| 10 | BPAC-5 | TEPO (76 ppb As) | 22° C. | 27.0 | 0.0 | 0 | 75.8 | NA |
|  |  |  |  | 30.0 | 10.0 | 24 | 23.3 | 0.47 |
|  |  |  |  | 30.0 | 10.0 | 48 | 9.0 | 0.60 |
|  |  |  | 80° C. | 27.0 | 0.0 | 0 | 75.8 | NA |
|  |  |  |  | 30.0 | 10.0 | 24 | 31.0 | 0.40 |
|  |  |  |  | 30.0 | 10.0 | 48 | 14.1 | 0.56 |
| 11 |  | TEPO (117 ppb As) | 22° C. | 27.0 | 0.0 | 0 | 117.3 | NA |
|  |  |  |  | 30.0 | 10.0 | 24 | 59.0 | 0.53 |
|  |  |  |  | 30.0 | 10.0 | 48 | 15.5 | 0.92 |
|  |  |  | 80° C. | 27.0 | 0.0 | 0 | 117.3 | NA |
|  |  |  |  | 30.0 | 10.0 | 24 | 55.6 | 0.56 |
|  |  |  |  | 30.0 | 10.0 | 48 | 20.6 | 0.87 |
| 12 | BPAC-6 | TEPO (76 ppb As) | 22° C. | 27.0 | 0.0 | 0 | 75.8 | NA |
|  |  |  |  | 30.0 | 10.0 | 24 | 9.0 | 0.60 |
|  |  |  |  | 30.0 | 10.0 | 48 | 8.1 | 0.61 |
|  |  |  | 60° C. | 27.0 | 0.0 | 0 | 75.8 | NA |
|  |  |  |  | 30.0 | 10.0 | 24 | 7.2 | 0.62 |
| 13 |  | TEPO (117 ppb As) | 22° C. | 27.0 | 0.0 | 0 | 117.3 | NA |
|  |  |  |  | 30.0 | 10.0 | 24 | 11.4 | 0.95 |
|  |  |  |  | 30.0 | 10.0 | 48 | 11.1 | 0.96 |
|  |  |  | 60° C. | 27.0 | 0.0 | 0 | 117.3 | NA |
|  |  |  |  | 30.0 | 10.0 | 24 | 9.7 | 0.97 |
| 14 | BPAC-7 | TEPO (76 ppb As) | 22° C. | 27.0 | 0.0 | 0 | 75.8 | NA |
|  |  |  |  | 30.0 | 10.0 | 24 | 14.9 | 0.55 |
|  |  |  |  | 30.0 | 10.0 | 48 | 10.0 | 0.59 |
| 15 | BPAC-8 | TEPO (76 ppb As) | 22° C. | 27.0 | 0.0 | 0 | 75.8 | NA |
|  |  |  |  | 30.0 | 10.0 | 24 | 15.4 | 0.54 |
|  |  |  |  | 30.0 | 10.0 | 48 | 12.5 | 0.57 |

Example 16

Removal of Trace Arsenic from TEPO Using Variable Loading Levels of Adsorbent BPAC-2

Working within a nitrogen glovebox, 45.0 g of TEPO and 5.0 g of adsorbent BPAC-2 were placed sequentially into a 100 ml Pyrex bottle to prepare the TEPO with 10.0 wt. % adsorbent. The 5.0 wt. % adsorbent sample was prepared in a similar manner using 28.5 g of TEPO and 1.5 g of adsorbent. The 2.0 wt. % adsorbent sample was prepared using 29.4 g of TEPO and 0.6 g of adsorbent. The 1.0 wt. % adsorbent sample was prepared using 29.7 g of TEPO and 0.3 g of adsorbent. BPAC-2 was previously activated as described in Example 1. The TEPO was previously analyzed to contain 76 ppb of arsenic by ICP-MS. The four bottles were capped with Teflon-coated lids, and were periodically agitated over the course of one hour by swirling the liquid to ensure that the adsorbent pellets were uniformly wetted. The bottles were left in the glovebox at ambient temperature. Small aliquots were taken from the bottles after 1, 2 and 3 days for arsenic analysis by ICP-MS. The analysis showed that the arsenic content in the TEPO dropped from an initial value of 76 ppb to 6.4 ppb for the TEPO exposed to 10.0 wt. % adsorbent for 3 days. The arsenic content dropped from an initial value of 76 ppb to 9.2 ppb, 11.3 ppb, and 14.6 ppb for the samples exposed to 5.0, 2.0 and 1.0 wt. % adsorbent, respectively for 2 days at ambient temperature. The data are summarized in Table 4.

Example 17

Removal of Trace Arsenic from TEPO Spiked with TEASAT Using Variable Loading Levels of Adsorbent BPAC-2

TEPO spiked with 30 ppb of arsenic as TEASAT was used for this example. This sample of TEPO was analyzed to contain 117 ppb of arsenic. Working within a nitrogen glovebox, 45.0 g of TEPO and 5.0 g of adsorbent BPAC-2 were placed sequentially into a 100 ml Pyrex bottle to prepare the TEPO with 10.0 wt. % adsorbent. The 5.0 wt. % adsorbent sample was prepared in a similar manner using 28.5 g of TEPO and 1.5 g of adsorbent. The 2.0 wt. % adsorbent sample was prepared using 29.4 g of TEPO and 0.6 g of adsorbent. The 1.0 wt. % adsorbent sample was prepared using 29.7 g of TEPO and 0.3 g of adsorbent. BPAC-2 was previously activated as described in Example 1. The four bottles were capped with Teflon-coated lids, and were periodically agitated over the course of one hour by swirling the liquid to ensure that the adsorbent pellets were uniformly wetted. The bottles were left in the glovebox at ambient temperature. Small aliquots were taken from the bottles after 1, 2 and 3 days for arsenic analysis by ICP-MS. The analysis showed that the arsenic content in the TEPO dropped from an initial value of 117 ppb to 10.5 ppb for the TEPO exposed to 10.0 wt. % adsorbent for 3 days. The arsenic content dropped from an initial value of 117 ppb to 5.2 ppb, 7.5 ppb, and 21.4 ppb for the samples exposed to 5.0, 2.0 and 1.0 wt. % adsorbent, respectively for 2 days at ambient temperature. The data are summarized in Table 4.

TABLE 4

Effect of the Loading Level of an Adsorbent (BPAC-2)

| Example No. | Adsorbent | TEPO Soure | Temp | Scale (g) | Adsorbent loading (wt. %) | Time (hours) | Arsenic conc. (ppb) | Arsenic capacity (µg/g ads) |
|---|---|---|---|---|---|---|---|---|
| 16 | BPAC-2 | TEPO (76 ppb As) | 22° C. | 45.0 | 0.0 | 0 | 75.8 | NA |
|   |   |   |   | 50.0 | 10.0 | 24 | 7.9 | 0.61 |
|   |   |   |   | 50.0 | 10.0 | 72 | 6.4 | 0.62 |
|   |   |   |   | 28.5 | 0.0 | 0 | 75.8 | NA |
|   |   |   |   | 30.0 | 5.0 | 24 | 14.5 | 1.17 |
|   |   |   |   | 30.0 | 5.0 | 48 | 9.2 | 1.27 |
|   |   |   |   | 29.4 | 0.0 | 0 | 75.8 | NA |
|   |   |   |   | 30.0 | 2.0 | 24 | 21.2 | 2.68 |
|   |   |   |   | 30.0 | 2.0 | 48 | 11.3 | 3.16 |
|   |   |   |   | 29.7 | 0.0 | 0 | 75.8 | NA |
|   |   |   |   | 30.0 | 1.0 | 24 | 28.5 | 4.69 |
|   |   |   |   | 30.0 | 1.0 | 48 | 14.6 | 6.06 |
| 17 |   | TEPO (117 ppb As) | 22° C. | 45.0 | 0.0 | 0 | 117.3 | NA |
|   |   |   |   | 50.0 | 10.0 | 24 | 11.5 | 0.95 |
|   |   |   |   | 50.0 | 10.0 | 72 | 10.5 | 0.96 |
|   |   |   |   | 28.5 | 0.0 | 0 | 117.3 | NA |
|   |   |   |   | 30.0 | 5.0 | 24 | 9.4 | 2.05 |
|   |   |   |   | 30.0 | 5.0 | 48 | 5.2 | 2.13 |
|   |   |   |   | 29.3 | 0.0 | 0 | 117.3 | NA |
|   |   |   |   | 30.0 | 2.0 | 24 | 20.6 | 4.74 |
|   |   |   |   | 30.0 | 2.0 | 48 | 7.5 | 5.38 |
|   |   |   |   | 29.7 | 0.0 | 0 | 117.3 | NA |
|   |   |   |   | 30.0 | 1.0 | 24 | 38.2 | 7.83 |
|   |   |   |   | 30.0 | 1.0 | 48 | 21.4 | 9.50 |

Example 18

Removal of Trace Arsenic from 216 g Sample of TEPO Using a Two Step Process: (1) Static Adsorption with 10.0 wt. % Adsorbent BPAC-2; and (2) Flash Distillation Working within a nitrogen glovebox, 216 g of TEPO and 24.0 g of adsorbent BPAC-2 were placed sequentially into a 500 ml Pyrex bottle. BPAC-2 was previously activated as described in Example 1. The TEPO was previously analyzed to contain 76 ppb of arsenic by ICP-MS. The bottle was capped with a Teflon-coated lid, and was periodically agitated over the course of several hours by swirling the liquid to ensure that the adsorbent pellets were uniformly wetted. The bottle was kept at ambient temperature in the glovebox. After three days the liquid was decanted into a second Pyrex bottle to separate the liquid from the adsorbent beads. The decanted TEPO was divided into two equal portions: Fraction A and Fraction B. A small aliquot of liquid was taken from Fraction A for arsenic analysis. Fraction B was flash distilled using a rotory evaporator. A small aliquot of the distillate from Fraction B was taken for arsenic analysis. The arsenic content of the adsorbent treated samples before and after flash distillation was measured to be 8.2 ppb and 4.1 ppb, respectively.

Example 19

Removal of Trace Arsenic from 1070 g Sample of TEPO Using a Two Step Process: (1) Static Adsorption with 10.0 wt. % Adsorbent BPAC-2; and (2) Flash Distillation Working within a nitrogen glovebox, 1070 g of TEPO and 119 g of adsorbent BPAC-2 were placed sequentially into a 1.5 liter quartz bubbler equipped with inlet and outlet Teflon valve assemblies. BPAC-2 was previously activated as described in Example 1. The TEPO was previously analyzed to contain 76 ppb of arsenic by ICP-MS. The bubbler was periodically agitated over the course of several hours by swirling the liquid to ensure that the adsorbent pellets were uniformly wetted. The bubbler was kept at ambient temperature in the glovebox. After 5 days the liquid was decanted into a second Pyrex bottle to separate the liquid from the adsorbent beads. The decanted TEPO was divided into two portions: Fraction A (~770 g) and Fraction B (~300 g). A small aliquot of liquid was taken from Fraction A for arsenic analysis. Fraction B was flash distilled using a rotory evaporator. A small aliquot of the distillate from Fraction B was taken for arsenic analysis. The arsenic content of the adsorbent treated samples before and after flash distillation was measured to be 8.5 ppb and 2.5 ppb, respectively.

Example 20

Removal of Trace Arsenic from 216 g Sample of TEPO Using a Two Step Process: (1) Static Adsorption with 10.0 wt. % Adsorbent BPAC-4; and (2) Flash Distillation Working within a nitrogen glovebox, 216 g of TEPO and 24.0 g of adsorbent BPAC-4 were placed sequentially into a 500 ml Pyrex bottle. BPAC-4 was previously activated as described in Example 1. The TEPO was previously analyzed to contain 76 ppb of arsenic by ICP-MS. The bottle was capped with a Teflon-coated lid, and was periodically agitated over the course of several hours by swirling the liquid to ensure that the adsorbent pellets were uniformly wetted. The bottle was kept at ambient temperature in the glovebox. After three days the liquid was decanted into a second Pyrex bottle to separate the liquid from the adsorbent beads. The decanted liquid was divided into two equal portions: Fraction A and Fraction B. A small aliquot of liquid was taken from Fraction A for arsenic analysis. Fraction B was flash distilled using a rotory evaporator. A small aliquot of the distillate from Fraction B was taken for arsenic analysis. The arsenic content of the adsorbent treated samples before and after flash distillation was measured to be 8.2 ppb and 4.1 ppb, respectively.

Example 21

Removal of Trace Arsenic from 1070 g Sample of TEPO Using a Two Step Process: (1) Static Adsorption with 10.0 wt. % Adsorbent BPAC-4; and (2) Flash Distillation Working within a nitrogen glovebox, 1070 g of TEPO and 119 g of DD-710 beads were placed sequentially into a 1.5 liter quartz bubbler equipped with inlet and outlet Teflon valve assemblies. Adsorbent BPAC-4 was previously activated as described in Example 1. The TEPO was previously analyzed to contain 76 ppb of arsenic by ICP-MS. The bubbler was periodically agitated over the course of several hours by swirling the liquid to ensure that the adsorbent pellets were uniformly wetted. The bubbler was kept at ambient temperature in the glovebox. After 6 days the liquid was decanted into a second Pyrex bottle to separate the liquid from the adsorbent beads. The decanted TEPO was divided into two portions: Fraction A (~770 g) and Fraction B (~300 g). A small aliquot of liquid was taken from Fraction A for arsenic analysis. Fraction B was flash distilled using a rotory evaporator. A small aliquot of the distillate from Fraction B was taken for arsenic analysis. The arsenic content of the adsorbent treated samples before and after flash distillation was measured to be 4.7 ppb and 0.5 ppb, respectively.

Example 22

Removal of Trace Arsenic from TEPO Using Adsorbent BPAC-10

A sample of MgO■$(K_2CO_3)_2$ supported on alumina, referred to herein as BPAC-10, was prepared by impregnating an aqueous solution containing dissolved magnesium acetate tetrahydrate ($Mg(OAc)_2$■$4H_2O$) and potassium acetate (KOAC) into a porous alumina substrate. To prepare the 4:1 K:Mg oxycarbonate, one would need to use a weight ratio of approximately 35 wt. % $Mg(OAc)_2$■$4H_2O$ to 65 wt. % KOAc to prepare the aqueous solution. The impregnated alumina substrate, prepared in the manner described, was subsequently calcined at 550° C. for 4 hours. Approximately 3.31 g of adsorbent BP-10 thus prepared was added to 23.45 g of TEPO in a 40 ml glass vial. After a 24 hour soak test, a sample of the treated TEPO was set aside for arsenic analysis. The before and after analysis showed that the arsenic dropped by approximately 20% from 109 ppb to 85 ppb.

Another sample of adsorbent BPAC-10 was prepared, this time calcining the impregnated alumina beads overnight at 430° C. The calcination was carried out for a longer period of time to remove free water, crystalline water, and to convert the $Mg(OAc)_2$ to MgO and the KOAc to $K_2CO_3$ in an attempt to produce a final supported material of the approximate composition of MgO■$(K_2CO_3)_2$ on $Al_2O_3$. Another soak test was done using a weight ration of 4.1:1 of TEPO to the alumina supported adsorbent. After 24 hours the TEPO was sampled showing that the arsenic was reduced by 80% to 22 ppb.

Example 23

Removal of Trace Arsenic from TEPO Using Adsorbents IE-1, AC-1 and SG-1

Additional screening of alternative absorbents was performed with the same TEPO raw material feed stock used in Example 22 (arsenic concentration of 109 ppb). TEPO was transferred into a 40 ml vial to about half volume. The vials had been prefilled with about 15 volume % of the adsorbent, which accounts for the variable weight ratios. Using a 13.27 weight ratio of TEPO to adsorbent, adsorbent IE-1 reduced the arsenic by 12% to 96 ppb. Adsorbent AC-1 reduced the arsenic by 43% to 62 ppb using a weight ratio of 5.883 of TEPO to adsorbent. The treatment with adsorbent SG-1 (8.398:1 weight ratio of TEPO to gel) had no influence on the arsenic level. Adsorbents IE-1, AC-1 and SG-1 are all non-alumina adsorbents, described in further detail in Table 1.

Example 24

Removal of Trace Arsenic from 26 g of TEPO Using BPAC-9

An adsorbent consisting of a 20:56:24 mixture of $K_2CO_2$: $MgO:Al_2O_3$ was used for this experiment. This adsorbent is referred to herein as BPAC-9. The raw TEPO used for this experiment was analyzed to contain 117 ppb arsenic. Adsorbent BP-9 was used as received from the vendor without any further activation. Working within a nitrogen glovebox, 26.5916 g of TEPO was placed into a 40 ml glass vial fitted with a screw-top cap. The vial was removed from the glovebox. 5.0572 g of BP-9 was added to the vial under ambient air conditions, corresponding to a ~5:1 weight ratio of TEPO to BPAC-9 adsorbent. The glass vial was agitated to mix several times over a minute or two, and then allowed to sit overnight. Approximately 24 hours later the vial was returned to the glovebox and 4 ml of the TEPO was separated from adsorbent BPAC-9 and filtered through a 0.45 micron syringe filter and submitted for arsenic analysis. Results indicated that the arsenic level in the filtered sample was 16.7 ppb, thus reducing the arsenic concentration by more than 85%.

Example 25

Removal of Trace Arsenic from TEPO Using BPAC-9 Adsorbent Using 16 kg of TEPO

Raw TEPO with an arsenic concentration of 85.2 ppb was used for this example. 16 kg of TEPO was transferred into each of two stainless steel vessels that contained 1.6 kg of BPAC-9 adsorbent to give a 10:1 weight ratio of TEPO to BPAC-9. The vessels were filled under vacuum and left under a reduced pressure headspace. Vessels were briefly agitated by rolling on the floor to optimize TEPO contact with the pellets. The third day after filling (approximately 72 hours contact time), the two vessels were sampled. An ampoule was pulled from each vessel containing about 50 mls of liquid. The two ampoules were taken into the glovebox and 4 mls of each sample was filtered through a 0.45 micron filter. Results for the two vessels indicated the first at 2.378 ppb and the second was 0.982 ppb. In this case, basically all the arsenic was removed from the TEPO, unfortunately, the TEPO increased in both potassium and sodium significantly. Potassium increased to 187 ppb and 161 ppb respectively and sodium up to 10.44 and 8.64 ppb. Typical levels for both elements in untreated raw material are less than 1 ppb.

Example 26

Purification of TEPO Containing High Levels of Arsenic Using BPAC-2 and BPAC-4 Adsorbents Working within a nitrogen glovebox, 18.0 g of TEPO and 2.0 g of adsorbent BPAC-2 were placed sequentially into a 50 ml Pyrex bottle. 18.0 g of TEPO and 2.0 g of adsorbent BPAC-4 were placed into a second Pyrex bottle. Adsorbents BPAC-2 and BPAC-4 were previously activated as described in Example 1. The TEPO was previously analyzed to contain over 10,000 ppb of arsenic by ICP-MS. The bottles were capped with Teflon-coated lids, and were periodically agitated over the course of one hour by swirling the liquid to ensure that the adsorbent pellets were uniformly wetted. The bottles were left in the glovebox at ambient temperature for 3 days, after which time small aliquots were removed for arsenic analysis by ICP-MS. The analysis showed that the arsenic content in the TEPO dropped from an initial value of over 10,000 ppb to 23 ppb for TEPO treated with BPAC-2, and to 97 ppb for TEPO treated with BPAC-4. This corresponds to removal of 99.8% and 99.0% of the arsenic for the samples treated with BPAC-2 and BPAC-4, respectively.

Example 27

Purification of TEPO Containing High Levels of Arsenic Using BPAC-2 and BPAC-4 Adsorbents TEPO spiked with 3,300 ppb of arsenic as TEASAT (triethylarsenate) was used for this example. Working within a nitrogen glovebox, 18.0 g of TEPO and 2.0 g of adsorbent BPAC-2 were placed sequentially into a 50 ml Pyrex bottle. 18.0 g of TEPO and 2.0 g of adsorbent BPAC-4 were placed into a second Pyrex bottle. Adsorbents BPAC-2 and BPAC-4 were previously activated as described in Example 1. The bottles were capped with Teflon-coated lids, and were periodically agitated over the course of one hour by swirling the liquid to ensure that the adsorbent pellets were uniformly wetted. The bottles were left in the glovebox at ambient temperature for 3 days, after which time small aliquots were removed for arsenic analysis by ICP-MS. The analysis showed that the arsenic content in the TEPO dropped to 11 ppb for TEPO treated with BPAC-2, and to 20 ppb for TEPO treated with BPAC-4. This corresponds to removal of 99.7% and 99.4% of the arsenic for the samples treated with BPAC-2 and BPAC-4, respectively.

The embodiments of this invention listed above, including the working example, are exemplary of numerous embodiments that may be made of this invention. It is contemplated that numerous other configurations of the process may be used, and the materials used in the process may be elected from numerous materials other than those specifically disclosed.

The invention claimed is:

1. A method of removing arsenic-containing impurities from raw triethylphosphate having the arsenic-containing impurities, comprising:
   providing an adsorbent selective to adsorb the arsenic-containing impurities with triethylphosphate;
   contacting the raw triethylphosphate having the arsenic-containing impurities with the adsorbent; and
   adsorbing the arsenic-containing impurities from the raw triethylphosphate having the arsenic-containing impurities to produce a product triethylphosphate having reduced arsenic-containing impurities.

2. The method of claim 1, wherein the adsorbent is an alumina containing adsorbent.

3. The method of claim 2, wherein the alumina containing adsorbent is a base promoted alumina containing adsorbent.

4. The method of claim 3, wherein the base promoted alumina containing adsorbent is represented by a formula: $Z_xW_y$; wherein x is weight percentage of Z in the adsorbent ranging from 30% to 99.999%;

y is weight percentage of W in the adsorbent, and x+y=100%;

Z is selected from the group consisting of alumina ($Al_2O_3$), magnesium-alumina based layered double hydroxide (MgO—$Al_2O_3$), alumina-zeolite, and mixtures thereof; and W is selected from the group consisting of at least one basic metal oxide, at least one basic metal carbonate, and mixtures thereof.

5. The method of claim 4, wherein the at least one basic metal oxide is at least one basic alkali metal, and the at least one basic metal carbonate is at lease one basic alkali metal carbonate.

6. The method of claim 4, wherein W is selected from the group consisting of MgO, CaO, $Na_2O$, $K_2O$, $K_2CO_3$, $Na_2CO_3$, and mixtures thereof.

7. The method of claim 1, wherein the adsorbent comprises ion exchange resin or activated carbon.

8. The method of claim 1, wherein the contacting is performed at a temperature ranging from 0° C. to 140° C.

9. The method of claim 1, wherein the contacting is a static contacting.

10. The method of claim 1, wherein the contacting is a dynamic contacting, comprising passing the raw triethylphosphate through a column packed with the adsorbent.

11. The method of claim 1, wherein the adsorbent is activated through heating under vacuum or under a dry inert gas atmosphere before the contacting.

12. The method of claim 1, wherein the arsenic-containing impurities from the raw triethylphosphate having the arsenic-containing impurities is in the range of 50 ppb to 10,000 ppb, and the reduced arsenic-containing impurities in the product triethylphosphate having the reduced arsenic-containing impurities is less than 10 ppb.

13. A method of removing arsenic-containing impurities from raw triethylphosphate having the arsenic-containing impurities, comprising:
   providing an adsorbent selective to adsorb the arsenic-containing impurities with triethylphosphate;
   contacting the raw triethylphosphate having the arsenic-containing impurities with the adsorbent; and
   adsorbing the arsenic-containing impurities from the raw triethylphosphate having the arsenic-containing impurities to produce a product triethylphosphate having reduced arsenic-containing impurities; and
   distilling the product triethylphosphate having reduced arsenic-containing impurities to further remove the arsenic-containing impurities from the product triethylphosphate having reduced arsenic-containing impurities.

14. The method of claim 13, wherein the adsorbent is an alumina containing adsorbent.

15. The method of claim 14, wherein the alumina containing adsorbent is a base promoted alumina containing adsorbent.

16. The method of claim 15, wherein the base promoted alumina containing adsorbent is represented by a formula: $Z_xW_y$; wherein x is weight percentage of Z in the adsorbent ranging from 30% to 99.999%;

y is weight percentage of W in the adsorbent, and x+y=100%;

Z is selected from the group consisting of alumina ($Al_2O_3$), magnesium-alumina based layered double hydroxide ($MgO$—$Al_2O_3$), alumina-zeolite, and mixtures thereof; and W is selected from the group consisting of at least one basic metal oxide, at least one basic metal carbonate, and mixtures thereof.

17. The method of claim 16, wherein the at least one basic metal oxide is at least one basic alkali metal, and the at least one basic metal carbonate is at lease one basic alkali metal carbonate.

18. The method of claim 16, wherein W is selected from the group consisting of $CaO$, $MgO$, $Na_2O$, $K_2O$, $K_2CO_3$, $Na_2CO_3$, and mixtures thereof.

19. The method of claim 13, wherein the adsorbent comprises ion exchange resin or activated carbon.

20. The method of claim 13, wherein the contacting is performed at a temperature ranging from 0° C. to 140° C.

21. The method of claim 13, wherein the contacting is a static contacting.

22. The method of claim 13, wherein the contacting is a dynamic contacting, comprising passing the raw triethylphosphate through a column packed with the adsorbent.

23. The method of claim 13, wherein the adsorbent is activated through heating under vacuum or under a dry inert gas atmosphere before the contacting.

24. The method of claim 13, wherein the arsenic-containing impurities from raw triethylphosphate is in the range of 50 ppb to 10,000 ppb, and the arsenic-containing impurities in the product triethylphosphate after the distilling step is less than 10 ppb.

25. A method of removing arsenic-containing impurities from raw triethylphosphate have the arsenic-containing impurities comprising:
- providing an adsorbent selective to adsorb the arsenic-containing impurities with triethylphosphate;
- contacting the raw triethylphosphate having the arsenic-containing impurities with the adsorbent; and
- adsorbing the arsenic-containing impurities from the raw triethylphosphate having the arsenic-containing impurities to produce a product triethylphosphate having reduced arsenic-containing impurities; and
- distilling the product triethylphosphate having reduced arsenic-containing impurities to further remove the arsenic-containing impurities, and remove volatile organic byproducts and non-volatile residual metallic impurities from the product triethylphosphate having reduced arsenic-containing impurities.

* * * * *